(12) United States Patent
Perez

(10) Patent No.: US 6,436,262 B1
(45) Date of Patent: Aug. 20, 2002

(54) COMPACT CELL CLAMP FOR SLAB GEL PLATE ASSEMBLY

(75) Inventor: Evelio Perez, San Pablo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 09/556,239

(22) Filed: Apr. 24, 2000

(51) Int. Cl.[7] .............. C02F 1/40; C02F 11/00; C25B 11/00; C25B 13/00; G01N 27/27
(52) U.S. Cl. .......... 204/618; 204/467; 204/616; 204/466
(58) Field of Search ................ 204/467, 618, 204/616, 466

(56) References Cited

U.S. PATENT DOCUMENTS

| | | |
|---|---|---|
| 4,518,476 A | 5/1985 | Delony et al. |
| 4,732,657 A | 3/1988 | November et al. |
| 4,828,669 A * | 5/1989 | Hellman, Jr. ............ 204/618 |
| 5,112,470 A | 5/1992 | Sylvester |
| 5,520,790 A * | 5/1996 | Chopas et al. ............ 204/606 |
| 5,632,877 A | 5/1997 | Van Atta |
| 6,110,340 A * | 8/2000 | Lau et al. ................. 204/467 |
| 6,179,980 B1 * | 1/2001 | Aksberg .................... 204/616 |

FOREIGN PATENT DOCUMENTS

| | | |
|---|---|---|
| EP | 0 339 975 A2 | 11/1989 |
| EP | 0 684 467 A1 | 11/1995 |
| WO | WO 98/52031 | 11/1998 |
| WO | WO 99/53305 | 10/1999 |
| WO | WO 00/47984 | 8/2000 |

* cited by examiner

Primary Examiner—Jill Warden
Assistant Examiner—Jennine Brown
(74) Attorney, Agent, or Firm—Townsend and Townsend and Crew, LLP

(57) ABSTRACT

Parallel plate slab gel enclosures (slab gel cassettes) used for vertical slab gel electrophoresis are secured to a frame to form a chamber for an upper buffer solution, and the securement is achieved by a pair of clamps that compress the cassettes against the frame. The clamps are preferably mounted to the frame in a pivotal connection that enables the user to easily rotate the clamps in and out of their clamping positions. An additional preferred feature is a pin protruding from each clamp in a position causing the pint to move upward against the bottom of the cassette and push the cassette upwards as the clamp is being engaged. This is particularly useful for cassettes formed of plates of unequal height where the shorter plate fits under an inverse shoulder on a gasket which thereby seals against both plates.

6 Claims, 2 Drawing Sheets

COMPACT CELL CLAMP FOR SLAB GEL PLATE ASSEMBLY

BACKGROUND OF THE INVENTION

1. Field of the Invention

This invention relates to electrophoresis cells for slab gel electrophoresis.

2. Description of the Related Art

Electrophoresis in vertically oriented slab gels is a process that is widely used for separating mixtures of chemical and biological species, such as proteins, oligopeptides, polypeptides, nucleic acids, and oligonucleotides. Among the numerous advantages of using slab gels are the ability to perform analyses on multiple samples at the same time, the ease of loading samples by inserting them in wells formed along the top edge of the slab, and the ease of placing the top and bottom edges of the slab in contact with separate buffer solutions for connection with separate electrodes.

In most applications, the slab is most conveniently cast in a sandwich-type arrangement between two flat transparent plates which are often combined in a unit that is referred to as a parallel plate gel enclosure or cassette. In use, the cassette is mounted in an electrophoresis cell, which provides electrical contact between the exposed edges of the gel and each of two electrodes through buffer solutions that carry the electric current between the electrodes and through the gel. The cell must contain the two buffer solutions and keep them separate from each other while maintaining full liquid contact between each buffer solution and the top and bottom edges of the gel, respectfully, and yet permit the user to insert and remove the cassette for analysis. Various cell designs have been developed that enable the user to assemble and disassemble the cell quickly so that successive runs can be performed in a routine manner, and when assembling the cell to do so securely, which is of value since improper assembly can result in leakage and failed experiments and the result may be lost time and sometimes lost samples as well. One such cell design is disclosed in U.S. Pat. No. 5,632,877, entitled "Rapid Assembly Electrophoresis Cell for Slab Gels," inventor D. van Atta, issued May 27, 1997.

SUMMARY OF THE INVENTION

The present invention resides in a pair of clamps designed to secure a cassette or parallel plate gel enclosures in general to a frame in a manner that will form the cassette and frame into buffer chambers as part of an electrophoresis cell. One of the various objects of this invention is to provide clamps that serve this purpose and yet are compact in design and structure, with dimensions not much larger than those of the cassette itself. Another object is to provide clamps that are readily secured and released and that when secured will provide a leak-free assembly.

These and other objects are achieved by a clamp construction that includes a support plate supporting two grasping members in the form of panels, preferably parallel, extending from one side of the support plate, each grasping member extending substantially the full length of a lateral edge of the cassette. A gap separates the two grasping members, the gap being sufficiently large to receive the lateral edge of the cassette and the frame in a snug fit. The grasping members themselves are substantially rigid, and any flexibility is sufficiently resilient that they compress the cassette against the frame with enough pressure to provide a liquid-tight seal. In the case where the frame is designed for two cassettes, one on either side, the gap between the grasping members is sufficiently larger to receive both cassettes and frame. When one or more gaskets are used to provide liquid-tight contact between the cassette(s) and the frame, the gap between the grasping members is large enough to receive the cassette(s), the frame and the gasket(s), all in a snug fit. To facilitate the placement of the clamp over these components, the leading edges of the inner faces of the grasping members are beveled. The clamp can thus be slipped over the cassettes and frame and provide an immediate clamping effect. The clamp serves all these purposes while leaving the upper and lower edges of the cassette exposed for contact with the electrode buffer solutions.

Certain additional features are included in preferred embodiments of the invention. One of these is a pivotal mounting of each clamp to the frame so that each clamp can be rotated into and out of the clamping position in which the clamp engages the cassette. Another is a protrusion extending from either or both of the lateral faces of the clamp, the protrusion(s) operating in conjunction with the pivotal mounting to produce a cam effect to enhance the sealing of the cassette against the frame.

This invention also resides in an assembly that includes a frame, one or two cassettes, a pair of clamps as described above, and optionally one or two gaskets. These and other features, embodiments, objects, and advantages of the invention will be better understood from the description that follows.

DETAILED DESCRIPTION OF THE INVENTION AND SPECIFIC EMBODIMENTS

While the invention is susceptible to a wide range of shapes, arrangements, and structures, the fundamental concepts of the invention and the manner in which they may be implemented will be best understood by reference to a particular embodiment. The following description and the attached figures address such an embodiment.

Figure 1:
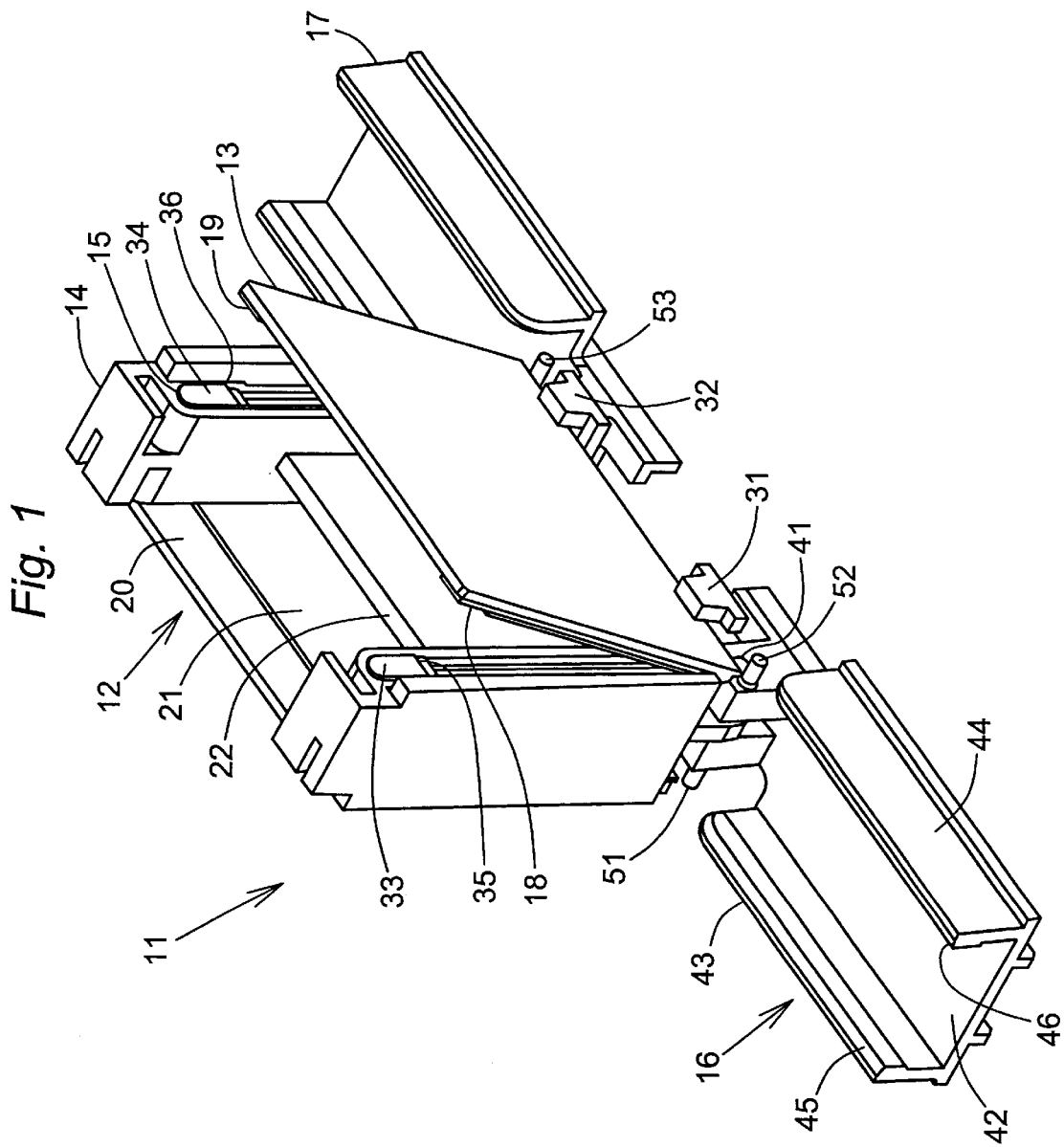
FIG. 1 is a perspective view of an assembly that includes a frame, two cassettes, and two clamps in accordance with this invention, the clamps being in an open position.

FIG. 1 shows an assembly 11 that includes two gel enclosures or cassettes 12, 13 mounted on a single frame 14 with gaskets (one of which 15 is visible), and a pair of clamps 16, 17, one to engage each of the two lateral edges of each cassette and to secure the cassettes along these lateral edges against the gasket and frame. The clamps 16, 17 are shown in an open position which allows the cassettes to be placed on the frame or removed from the frame.

Each cassette consists of two flat plates of unequal height, separated by thin spacers (18, 19) along the lateral edges of the plates or raised edges along one of the plates, in either case leaving a narrow gap between the plates that defines the thickness of the gel. The two plates are positioned such that the bottom and side edges of both plates are aligned, with the top edge of one plate extending a short distance above the top edge of the other plate. The difference in height between the tall and short plates is most readily seen in the rear cassette 12 where the tall plate 20 faces the exterior of the frame and the short plate 21 faces the interior. The forward cassette 13 is arranged in the opposite direction such that both tall plates are on the outside and both short plates on the inside. The frame itself is U-shaped, with an internal crossbar 22 for structural reinforcement. Thus, when the two cassettes are clamped to the frame, the cassettes and frame form a receptacle for the upper electrode buffer solution, and the tall plates serve as retaining walls for the solution with the liquid level of the solution being intermediate in height between the short and tall plates. An electrode (not shown) will extend across the frame under the liquid level.

While the embodiment shown in this Figure is designed to secure two cassettes to a common frame, a frame may also be used that will accommodate only one cassette and yet operate in substantially the same manner. Similarly, the frame shown in the Figure can also be used with a single cassette by substituting a dam for one of the cassettes, the dam having the same exterior shape as a cassette but solid in construction with neither a gel nor a gap. The dam thus serves as a retaining wall for the upper electrode buffer solution. The assembly shown in the Figure does not include a reservoir for the lower electrode buffer solution. As in the vertical electrophoresis cells of the prior art, notably that of U.S. Pat. No. 5,632,877 referenced above, the lower electrode and buffer solution are contained in a tank in which the cassette and frame assembly are inserted. The disclosure of U.S. Pat. No. 5,632,877 is incorporated herein by reference in its entirety.

Each of the cassettes rests on grooved tabs extending from the bottom of the frame 14. While only the two tabs 31, 32 for the front cassette are visible in the Figure, an identical pair extend from the opposite side for the rear cassette. The cassettes are manually lowered into and lifted from the grooves in these tabs by the user. The grooves permit the used to rotate the cassette away from the frame and they also serve as a guide for placing the enclosure in its proper position against the frame prior to clamping.

The gasket 15 is U-shaped and fits in a U-shaped groove on the forward face of the frame, sealing the bottom edge and the side edges of the cassette against the frame. The two upper ends 33, 34 of the gasket are slightly thicker than the remainder of the gasket, giving the gasket a stepped profile with inverted shoulders 35, 36 that face the cassette directly across from the top edge of the shorter plate. When the cassette is pressed against the gasket, the stepped profiles formed by the shoulders follow the stepped profile formed by the combination of the short and tall plates. This provides a liquid-tight seal extending from the shorter plate across the gap to the taller plate. An identical gasket is positioned on the other side of the frame, and therefore not visible in this drawing.

The two clamps 16, 17 are symmetrically arranged along the two lateral edges of the frame and the cassettes, and are shown in FIG. 1 in the open or non-clamping position to allow the cassettes to be inserted or removed. In this embodiment, both clamps are mounted directly to the frame 14 by pivot pins that extend through the base of the frame, only one pivot pin 41 being visible. Each clamp is generally C-shaped, with a back support plate 42 and two grasping walls or members 43, 44, each of which is sufficiently rigid to serve a clamping function. The inner edges of these grasping walls that first come into contact with the cassettes are beveled 45, 46 to facilitate entry.

Figure 2:
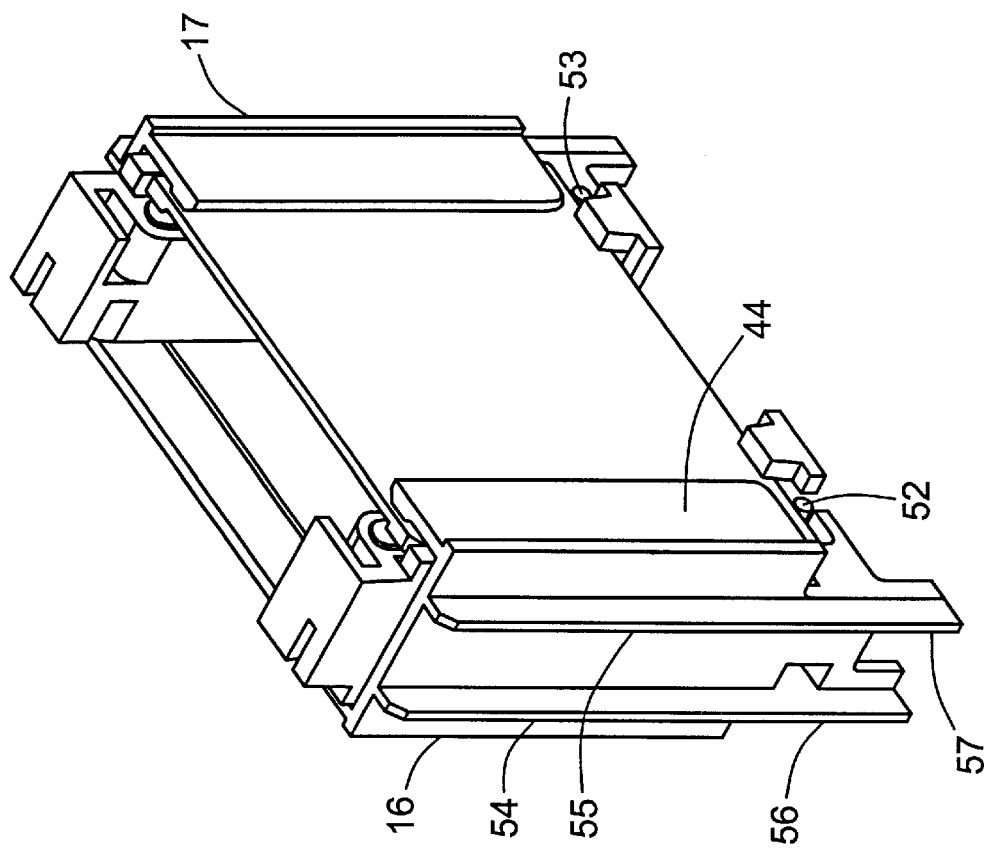
FIG. 2 is a perspective view of the assembly of FIG. 1 with the clamps in the closed position.

Below the grasping walls of each clamp are protrusions in the form of pins 51, 52, 53 (and a fourth that is not visible) that extend outward from the front and rear faces of the clamps in a direction parallel to the pivot axis and perpendicular to the planes of the cassettes. The pins are not coaxial with the pivot axis and therefore move around the pivot axis when the clamps are rotated. This movement causes the pins to act as cams, contacting the lower edges of the cassettes and urging the cassettes upward as the clamps are rotated into the clamping position (as shown in FIG. 2). The upward urging of the cassettes serves to press the upper edges of the short plates against the inverted shoulders on the gaskets, thereby securing the seal at that location. The positions of the pins can be arranged such that they pass through a maximum when moving between the open position and the clamping position, thereby stabilizing the clamp in the clamping position.

The same assembly is shown in the clamping position in FIG. 2, in which the clamps are rotated upward so that the grasping walls engage the two cassettes and press them against the frame with the gaskets in between. The clamps are constructed with ridges 54, 55 along their outer faces for structural reinforcement. Each clamp contains legs 56, 57 that extend below the frame when the clamps are in this position. These legs serve to raise the assembly above the floor of the tank in which the assembly is placed, leaving room beneath the cassettes for a cooling coil and a holder for the electrode that will serve as the lower electrode. The cooling coil and electrode holder are not shown in the Figure.

The foregoing is offered primarily for purposes of illustration. Further modifications and variations that fall within the scope of the invention will be readily apparent to those skilled in the art.

What is claimed is:

1. A pair of clamps for securing a parallel plate gel enclosure against a frame to form a liquid-retaining chamber for an electrophoresis buffer, each said clamp comprising a plate with a pair of flat extension members extending from one side of said plate with a gap between said extension members that is sized to receive said gel enclosure and said frame in a snug fit, said extension members extending substantially the full length of a lateral edge of said gel enclosure, each said extension member having an inner face terminating in a beveled edge to facilitate insertion of said lateral edge of said gel enclosure, each clamp pivotally mounted to said frame for rotation about a pivot axis between a clamping position in which said extension members compress said gel enclosure against a clamping surface on said frame, and an open position in which said extension members are displaced from said clamping surface to permit free insertion and removal of said gel enclosure to and from said frame, said clamp further comprising a protrusion positioned to engage a bottom edge of said gel enclosure and to urge said gel enclosure upward when said clamp is rotated into said clamping position.

2. Apparatus for performing slab gel electrophoresis in a vertical position, said apparatus comprising:
   a parallel plate gel enclosure;
   a frame; and
   a pair of clamps for securing said parallel plate gel enclosure against said frame, each said clamp comprising a plate with a pair of flat extension members extending from one side of said plate with a gap between said extension members that is sized to receive said gel enclosure and said frame in a snug fit, said extension members extending substantially the full length of a lateral edge of said gel enclosure, each said extension member having an inner face terminating in a beveled edge to facilitate insertion of said lateral edge of said gel enclosure, each clamp pivotally mounted to said frame for rotation about a pivot axis between a clamping position in which said extension members compress said gel enclosure against a clamping surface on said frame, and an open position in which said extension members are displaced from said clamping surface to permit free insertion and removal of said gel enclosure to and from said frame, each clamp further comprising a protrusion positioned to engage a bottom edge of one of said gel enclosures and to urge said gel enclosure upward when said clamp is rotated into said clamping position.

3. Apparatus in accordance with claim 2 further comprising two parallel plate gel enclosures, each said pair of extension members defining a gap that is sized to receive both gel enclosures and said frame in a snug fit.

4. Apparatus in accordance with claim 2 further comprising a gasket between said frame and said parallel plate gel enclosure.

5. Apparatus in accordance with claim 3 further comprising a pair of gaskets, one between said frame and each said parallel plate gel enclosure.

6. in accordance with claim 2 further comprising a pair of gaskets each having a stepped profile thereby forming an inverse shoulder, said protrusions positioned to engage a bottom edge of said gel enclosure and to urge said gel enclosure against said inverse shoulder.

* * * * *